(12) United States Patent
Denninghoff

(10) Patent No.: US 6,701,169 B1
(45) Date of Patent: Mar. 2, 2004

(54) METHOD OF DETERMINING AUTOREGULATORY AND PERFUSION STATUS

(75) Inventor: Kurt R. Denninghoff, Vestavia, AL (US)

(73) Assignee: The UAB Research Foundation, Birmingham, AL (US)

(*) Notice: Subject to any disclaimer, the term of this patent is extended or adjusted under 35 U.S.C. 154(b) by 0 days.

(21) Appl. No.: 10/018,261
(22) PCT Filed: Apr. 28, 2000
(86) PCT No.: PCT/US00/11466
§ 371 (c)(1),
(2), (4) Date: Nov. 6, 2001
(87) PCT Pub. No.: WO00/65986
PCT Pub. Date: Nov. 9, 2000

Related U.S. Application Data

(60) Provisional application No. 60/132,023, filed on Apr. 30, 1999.

(51) Int. Cl.[7] ................................................. A61B 5/00
(52) U.S. Cl. ....................................... 600/320; 600/328
(58) Field of Search ................................. 600/310, 318, 600/320, 322, 323, 324, 328, 340

(56) References Cited

U.S. PATENT DOCUMENTS

| 5,119,814 A | 6/1992 | Minnich ...................... 128/633 |
| 5,868,134 A | 2/1999 | Sugiyama et al. .......... 128/630 |

*Primary Examiner*—Eric F. Winakur
(74) *Attorney, Agent, or Firm*—Gifford, Krass, Groh, Sprinkle, Anderson & Citkowski, P.C.

(57) ABSTRACT

A method of determining the autoregulatory status of a subject by obtaining a measurement of a selected parameter of the retinal blood vessels in a non-stimulated subject, administering to the subject a preselected stimulus, obtaining a measurement of the selected parameter of the retinal blood vessels of the subject in response to the administration of the selected stimulus, and determining the ratio of the measurement for the selected parameter in the non-stimulated retinal blood vessels to the measurement of the selected parameter for the retinal blood vessels following the administration of its selected stimulus whereby the ratio provides an indicator of the autoregulatory function or status of the subject.

12 Claims, 1 Drawing Sheet

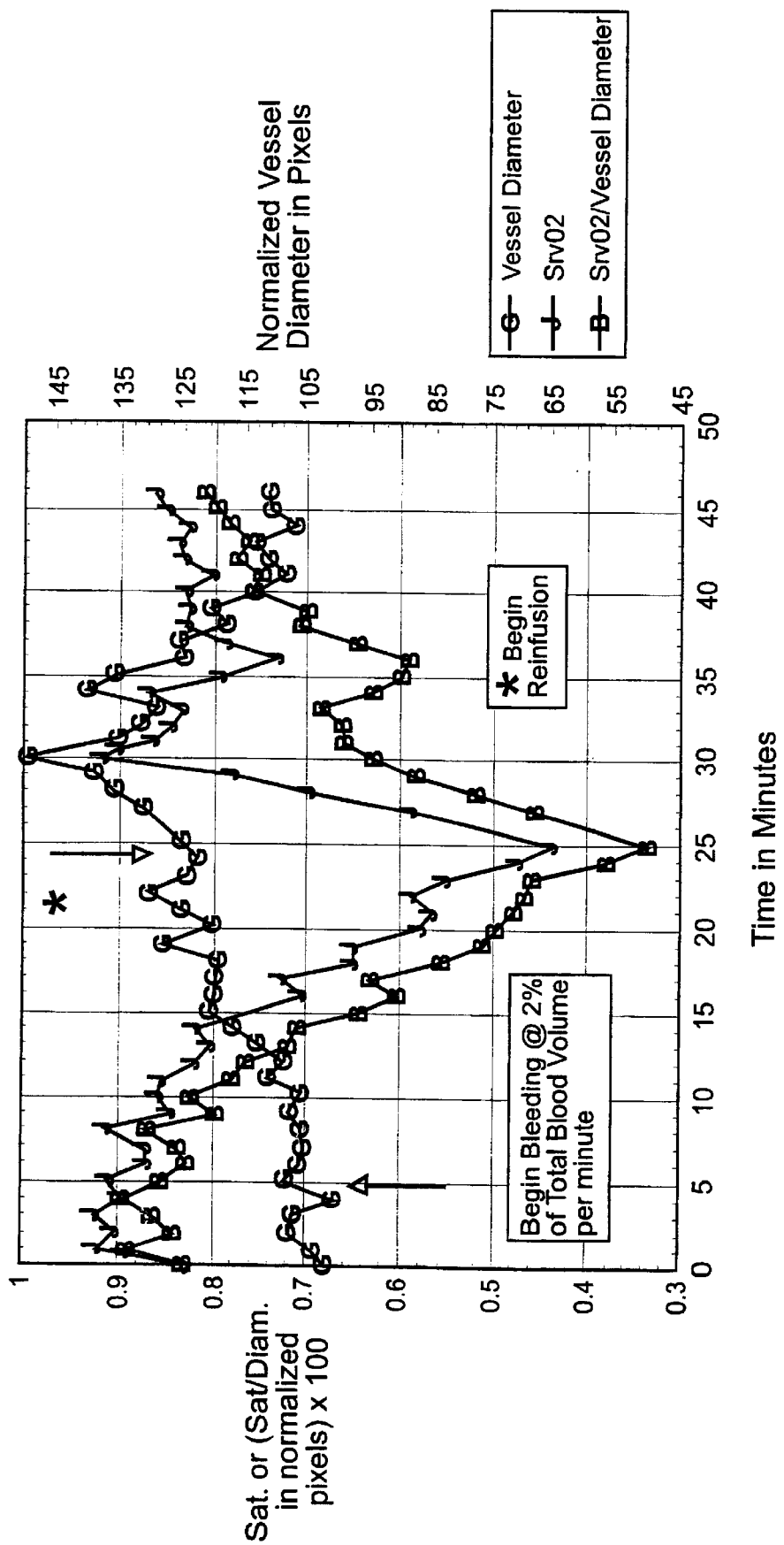

METHOD OF DETERMINING AUTOREGULATORY AND PERFUSION STATUS

This application claims benefit of Ser. No. 60/132,023 filed Apr. 30, 1999.

GRANT REFERENCE

The U.S. Government has a nonexclusive, nontransferable, irrevocable paid-up license to practice or have practiced this invention for or on its behalf as provided for by the terms of Contract DAMD17-98-1-8007 awarded by the U.S. Department of the Army.

TECHNICAL FIELD

The present invention relates to a method of determining the autoregulatory status of a subject. More specifically, the present invention relates to a method for measuring the autoregulatory status of a subject by noninvasively monitoring blood vessel changes in the retina.

BACKGROUND OF THE INVENTION

Local autoregulation is the physiologic phenomenon where the vascular bed attempts to match supply of substrate (primarily oxygen and glucose) and the removal of metabolic waste (primarily carbon dioxide and lactic acid) to the metabolic demand of the tissues by changing the resistance to flow therethrough. Resistance to flow is controlled by changes in blood vessel wall tension which changes the diameter of the blood vessels. When supply is generous, the blood vessels constrict decreasing flow. Conversely, when supply is limited, the blood vessels dilate increasing flow. Some of the substances which are known to change the autoregulatory state of tissues include oxygen, glucose, carbon dioxide and lactic acid.

Blood supply to the tissues is regulated by chemical signals transported throughout the body by the blood, by local metabolic demand, and by the autonomic nervous system which has nerve endings traveling with the blood vessels. Circulating substances generally regulate the balance of flow to the major organ systems of the body. An example of this is when a subject is bleeding and circulating catecholamines are released which shunt blood flow from the peripheral tissues to the central organs such as the brain and heart.

The retina is an embryologic extension of the brain and, as such, it is a centrally perfused organ and would not be expected to restrict flow in response to circulating substances released to maintain flow to the central circulation. The autonomic nerve endings which travel with the blood vessels in the body stop at the lamina cribosa prior to entering the retina. This allows the retinal circulation to respond to circulating chemical regulators and to local metabolic demand without interference from the autonomic nervous system. Accordingly, this characteristic makes the retina an ideal location for studying and assessing autoregulatory states by analyzing changes in the retinal blood vessel diameter and/or oxyhemoglobin saturation.

The analysis of retinal blood vessels to diagnose autoregulatory function/dysfunction can be useful in diagnosing and treating various diseases which have an autoregulatory dysfunction as a component of the disease. Examples of such diseases include diabetes, hypertension and glaucoma.

Glaucoma accounts for between 9% and 12% of all cases of blindness in the United States. Between two and three million people aged forty and older have glaucoma, and between 89,000 and 120,000 are blind from it. Glaucoma was originally believed to be a problem of elevated intraocular pressure (IOP) causing damage to the optic nerve. It is now clear that glaucoma clinically is a heterogenous collection of disorders with a similar clinical course and presentation. There are many treatment modalities for glaucoma, yet all are designed to do only one thing—lower IOP. Without treatment there is a relentless course of progressive visual loss. Unfortunately, many people have continued progression even when treatment is believed to have stabilized IOP in the normal range. This finding coupled with the fact that approximately one-third of glaucoma patients have normal IOP or Normal Tension Glaucoma (NTG) has led to exploration of other etiologies, such as vascular causes. A vascular role was initially suggested because of the association of glaucoma with systemic vascular diseases such as hypertension, migraine, diabetes and peripheral vascular disease. In addition, the presence of disk hemorrhages and retinal vein occlusions early in the glaucomatous disease process supports the vascular theory.

Although research on the vascular theories of glaucoma have focused on autoregulation, many of the parameters related to the blood vessel size, shape and blood flow hemodynamics have been difficult to quantify. Color Doppler Imaging (CDI) has been used to measure the peak blood flow velocity in the ocular blood vessels. These studies have demonstrated that blood velocity is decreased in the ophthalmic artery, posterior ciliary artery and central retinal artery of glaucoma patients.

Quantification of the vascular aspects of glaucoma has been difficult due to our limited knowledge of blood flow hemodynamics and autoregulatory mechanisms in the eye. Because there is no autonomic innervation of the retinal circulation distal to the lamina cribosa, autoregulatory mechanisms in the retina are controlled locally. Several studies have concluded that autoregulation in normal patients is similar to the autoregulation in ocular hypertensive patients, but autoregulation in glaucoma patients is insufficient.

Accordingly, it would be both advantageous and desirable to have a rapid, noninvasive method for measuring the retinal autoregulatory status of a subject in order to obtain information regarding the subject's condition which will be useful in the diagnosis and treatment of conditions having an autoregulatory component including glaucoma.

BRIEF DESCRIPTION OF THE DRAWINGS

The following detailed description is best understood with reference to the following drawings in which:

FIG. 1 is a graph illustrating changes in the autoregulatory state of the retinal during bleeding and resuscitation.

DETAILED DESCRIPTION OF THE INVENTION

The present invention provides a method of determining or monitoring the autoregulatory status of a subject, including humans and animals, by obtaining a measurement of a selected parameter of retinal blood vessels in a non-stimulated subject. As defined herein, "non-stimulated" refers to a subject in a normal or static condition who has not received any particular stimulus or substrate and/or inducing treatment. The subject can then be administered a preselected stimulus or substrate such as oxygen, glucose, carbon dioxide, lactic acid, or other circulating substances such as epinephrine. After the administration of the preselected stimulus or substrate, a measurement of the selected parameter of the retinal blood vessels of the subject is taken in order to determine the response of the subject to the administration of the selected stimulus or substrate. The changes in the autoregulatory state of the vascular bed can be determined by comparing the ratio of the measurement for the selected parameter in the retinal blood vessels of the non-stimulated subject to the measurement of the selected parameter for the retinal blood vessels following the administration of the selected stimulus or substrate in order to identify imbalances between the supply and consumption of the stimulus or substrate.

Normal autoregulatory function is defined herein as a balance between the stimulus or substrate supply and its consumption as determined by measurement techniques including retinal analysis.

The preselected parameters can include measuring the oxygen saturation of the retinal blood vessels, measuring the diameter of the retinal blood vessels, a combination of both and/or other parameters. Measurement of the selected parameters can be accomplished by utilizing a laser eye oximeter (EOX) which is directly aimed into the eye, much like an ophthalmoscope, and which will take readings (pictures) of the retina. The EOX is preferably an r-wave triggered laser scanning device which measures the blood vessel diameters near the optic disk of the retina and can accurately measure the oxygen saturation in the retinal artery and vein by measuring the saturations in the artery/vein pair near the optic disk. Suitable EOX devices include those disclosed in U.S. Pat. Nos. 5,119,814 and 5,308,919 to Minnich.

The measurements of the selected parameters can be used to calculate a ratio which is indicative of the balance or imbalance of the autoregulatory function of the subject or individual.

Changes in the autoregulatory state of a vascular bed can be monitored by monitoring the changes in the vessel diameter and the balance between substrate supply and consumption. The autoregulatory status can be calculated based on the data obtained from the retinal blood vessels.

Vessel Diameter Changes

Measuring the vessel diameter (D) changes when a subject is breathing oxygen ($D_{o2}$) and when they are on room air ($D_a$) yields a ratio which is related to the autoregulatory responsiveness of those tissues. This expressed by the equation:

$$AS \propto D_a/D_{o2}$$

The Ratio of Oxygen Consumption to Delivery

Effective autoregulation of blood supply balances the supply of oxygen with tissue oxygen demand. Thus, when oxygen delivery changes, vascular tone also changes maintaining the oxygen supply to the tissue.

The autoregulatory state can be quantified by measuring the change in substrate (oxygen) delivery to the tissue and substrate (oxygen) consumption. Oxygen consumption is equal to the blood flow volume (V) times the arteriovenous oxygen difference. The oxygen content of arterial blood ($C_aO_2$) is defined by the equation:

$$C_aO_2=[Hb](1.34)(S_aO_2/100)+(P_aO_2)(0.003)$$

wherein [Hb] is the hemoglobin concentration in grams per deciliter of blood, $S_aO_2$ is the percent oxygen saturation of hemoglobin in the arterial blood, and $P_aO_2$ is the partial pressure of oxygen in the arterial plasma. Thus the arteriovenous oxygen difference ($\Delta_{av}O_2$) is defined by the equation:

$$\Delta_{av}O_2=[Hb](1.34)((S_aO_2-S_vO_2)/100)+(P_aO_2-P_vO_2)(0.003)$$

wherein $S_vO_2$ is the percent oxygen saturation of hemoglobin in the venous blood and $P_vO_2$ is the partial pressure of oxygen in the venous plasma. Oxygen consumption and oxygen delivery can be estimated by assuming that the plasma contribution to oxygen delivery is negligible under isobaric conditions. The equation is:

$$\text{Oxygen consumption} \cong V(\Delta_{av}O_2) \cong V([Hb](1.34)(S_aO_2-S_vO_2)/100)$$

$$\text{Oxygen delivery} \cong V(C_aO_2) \cong V([Hb](1.34)(S_aO_2/100))$$

The ratio of oxygen consumption to oxygen delivery is a measure of the autoregulatory state (AS) of the tissue and can be estimated using the equation:

$$AS \cong V([Hb](1.34)((S_aO_2-S_vO_2)/100))/V([Hb](1.34)(S_aO_2/100))$$

Dividing out common terms gives the equation:

$$AS \cong (S_aO_2-S_vO_2)/S_aO_2.$$

A typical test to determine the autoregulatory status of an individual can include, for example, taking a measurement of the oxygen saturation of the retinal blood vessels with the EOX while the subject is breathing room air. The subject will then be scanned utilizing the EOX device while breathing supplemental oxygen (e.g., 15 liters/minute via non-rebreather mask). The measurements obtained by the EOX scan are analyzed to generate a ratio of the non-stimulated to stimulated oxygen saturation levels to determine whether a balance or imbalance exists and, thus, when an autoregulatory imbalance exists.

This method can be adapted for the diagnosis and/or monitoring of subjects with glaucoma using the EOX to measure retinal arterial and venous oxygen saturation during normoxia (un-stimulated) and hyperoxia (stimulated) conditions. An imbalance in the levels of stimulus/substrate delivery and consumption are utilized to ascertain autoregulatory function and/or dysfunction. In addition to glaucoma diagnosis and monitoring, the present method can also be utilized to diagnose and/or monitor other diseases with a component of autoregulatory dysfunction including diabetes and hypertension.

Measurements of retinal vessel parameters can also be used to monitor a patient or subject for blood loss during resuscitation from blood loss, during transfusions, during surgery or during the treatment of anemia or traumatic injury.

The ratio of retinal venous oxygen saturation to retinal venous diameter can be utilized for this purpose.

Because the present methods provide for quick, non-invasive, and accurate measurements of the autoregulatory status of a subject, they provide a new and valuable clinical tool for the diagnosis, treatment, and/or monitoring of diseases or conditions associated with autoregulatory dysfunction.

The EOX has been used to monitor the changes in retinal venous oxygen saturation and retinal venous diameter during the removal of forty percent of the blood and the subsequent reinfusion of blood in six swine. The results of this study are shown in FIG. 1 and demonstrate that the retinal venous oxygen saturation decreased during blood removal and returned to near normal levels rapidly after reinfusion of blood was initiated and that the retinal vessel diameter increased during blood removal and generally decreased during reinfusion of blood. The retinal venous oxygen saturation divided by the retinal venous diameter demonstrated the highest correlation with blood volume (r=0.9), emphasizing the importance of the autoregulatory state as defined herein.

In view of the teaching presented herein, other modifications and variations of the present invention will readily be apparent to those of skill in the art. The discussion and description are illustrative of some embodiments of the present invention, but are not meant to be limitations on the practice thereof. It is the following claims, including all equivalents, which define the scope of the invention.

Any patents or publications mentioned in the specification are indicative of the levels of those skilled in the art to which the invention pertains. These patents and publications are herein incorporated by reference to the same extent as if each individual publication was specifically and individually indicated to be incorporated by reference.

What is claimed is:

1. A method of determining the autoregulatory status of a subject, said method comprising the steps of:

obtaining a measurement of a selected parameter of the retinal blood vessels in a non-stimulated subject;

administering to the subject a preselected stimulus;

obtaining a measurement of the selected parameter of the retinal blood vessels of the subject in response to the administration of the selected stimulus; and determining the ratio of the measurement for the selected parameter in the non-stimulated retinal blood vessels to the measurement of the selected parameter for the retinal blood vessels following the administration of the selected stimulus whereby the ratio provides an indicator of the autoregulatory function or status of the subject.

2. A method according to claim 1, wherein said obtaining steps further comprise measuring the selected parameter with a laser scanning device.

3. A method according to claim 1, wherein the selected parameter comprises oxygen saturation of the retinal blood vessels.

4. A method according to claim 1, wherein the selected parameter comprises retinal blood vessel diameter.

5. A method according to claim 1, wherein the preselected parameter includes both oxygen saturation and blood vessel diameter in retinal blood vessels.

6. A method according to claim 1, wherein the preselected stimulus is 100% oxygen.

7. A method according to claim 1, wherein the preselected stimulus is selected from the group consisting of glucose, lactic acid, and carbon dioxide.

8. A method according to claim 1, wherein said determining step further comprises calculating the autoregulatory state using the equation:

$$\text{autoregulatory state} \cong (S_aO_2 - S_vO_2)/S_aO_2,$$

wherein $S_aO_2$ is the percent oxygen saturation of hemoglobin in arterial blood and $S_vO_2$ is the percent oxygen saturation in venous blood.

9. A method of diagnosing and monitoring glaucoma in a subject by assessing autoregulatory function, said method comprising the steps of:

measuring the venous oxygen saturation level of retinal blood vessels of a subject under normoxic conditions;

measuring the venous oxygen saturation level of the retinal blood vessels of the subject under hyperoxic conditions; and determining the ratio of the normoxic venous oxygen saturation level to the hyperoxic venous oxygen saturation level, wherein the ratio provides an indicator of the autoregulatory or status of the subject which can be used to diagnose and/or monitor the subject for glaucoma.

10. A method according to claim 9 further including the step of administering oxygen to the subject to induce the hyperoxic condition.

11. A method according to claim 9, wherein said determining step further comprises calculating the autoregulatory state using the equation:

$$\text{autoregulatory state} \cong (S_aO_2 - S_vO_2)/S_aO_2,$$

wherein $S_aO_2$ is the percent oxygen saturation of hemoglobin in arterial blood and $S_vO_2$ is the percent oxygen saturation in venous blood.

12. A method of monitoring blood loss in a subject, said method comprising the steps of:

measuring of retinal venous oxygen saturation;

measuring retinal venous diameter; and calculating the ratio of the measurement of retinal venous oxygen saturation to retinal venous diameter wherein the ratio provides an indicator of the amount of blood loss in the subject.

* * * * *

UNITED STATES PATENT AND TRADEMARK OFFICE
CERTIFICATE OF CORRECTION

PATENT NO. : 6,701,169 B1
DATED : March 2, 2004
INVENTOR(S) : Kurt R. Denningoff It is certified that error appears in the above-identified patent and that said Letters Patent is hereby corrected as shown below:

Column 5,
Line 35, replace "whereby" with -- wherein --.
Line 36, after "autoregulatory", delete -- function or --.

Signed and Sealed this

Eighth Day of February, 2005

JON W. DUDAS
*Director of the United States Patent and Trademark Office*